US 6,647,291 B1

(12) United States Patent
Bonner et al.

(10) Patent No.: US 6,647,291 B1
(45) Date of Patent: Nov. 11, 2003

(54) METHOD AND APPARATUS FOR CARDIAC DEFIBRILLATION

(75) Inventors: Matthew D. Bonner, Plymouth, MN (US); Rahul Mehra, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/540,136

(22) Filed: Mar. 31, 2000

Related U.S. Application Data
(60) Provisional application No. 60/127,758, filed on Apr. 5, 1999.

(51) Int. Cl.⁷ .................................................. A61N 1/18
(52) U.S. Cl. .......................................... 607/5; 607/123
(58) Field of Search ..................................... 604/5, 123

(56) References Cited

U.S. PATENT DOCUMENTS

| | | | |
|---|---|---|---|
| 5,261,400 A | 11/1993 | Bardy | 607/5 |
| 5,447,519 A | 9/1995 | Peterson | 607/5 |
| 5,476,498 A | 12/1995 | Ayers | 607/122 |
| 5,531,781 A | 7/1996 | Alferness et al. | 607/122 |
| 5,755,765 A | 5/1998 | Hyde et al. | 607/122 |
| 5,755,766 A | 5/1998 | Chastain et al. | 607/122 |
| 5,797,967 A | 8/1998 | KenKnight | 607/4 |
| 5,800,464 A | 9/1998 | Kieval | 607/9 |
| 5,800,495 A | 9/1998 | Machek et al. | 607/116 |
| 5,803,928 A | 9/1998 | Tockman et al. | 607/122 |
| 5,836,975 A | 11/1998 | DeGroot | 607/5 |
| 5,935,160 A | 8/1999 | Auricchio et al. | 607/122 |
| 5,978,704 A * | 11/1999 | Ideker et al. | 607/5 |
| 6,205,357 B1 * | 3/2001 | Ideker et al. | 607/14 |
| 6,243,603 B1 * | 6/2001 | Ideker et al. | 607/5 |

* cited by examiner

Primary Examiner—Mark Bockelman
(74) Attorney, Agent, or Firm—Girma Wolde-Michael; Daniel G. Chapik

(57) ABSTRACT

A method for cardioverting or defibrillating a human heart, performed by placing a transvenous lead having a cardioversion or defibrillation electrode such that the electrode is located at least partially within the middle cardiac vein of a patient's heart and placing an additional cardioversion or defibrillation electrode in the superior vena cava of the patient's heart and thereafter delivering a cardioversion or defibrillation pulse between the first and second electrodes. The method may be practiced by placing the transvenous such that the defibrillation electrode it carries extends around the apex of the patient's heart, and the transvenous lead may be advanced through one cardiac vein toward the apex of the patient's heart and thereafter advanced upward through a different cardiac vein.

21 Claims, 3 Drawing Sheets

METHOD AND APPARATUS FOR CARDIAC DEFIBRILLATION

This application claims priority from Provisional Application No. 60/127,758, filed Apr. 5, 1999.

BACKGROUND OF THE INVENTION

Over the past few years there has been an increased interest in the ability to place defibrillation leads in the cardiac veins, and in particular in placing small diameter defibrillation electrodes in more apical locations within the cardiac venous system. For example, U.S. Pat. Nos. 5,755,766, 5,803,928, and 5,755,765 all disclose cardiac vein leads adapted to be placed within the cardiac venous system by means of a guidewire passing through a portion of the lead or passing through a guide mounted to the lead. In the context of these leads, the guidewire is first advanced through the cardiac venous system to the desired point of implant and the lead is thereafter advanced down the guidewire, to its desired ultimate location. In addition, it has been proposed to provide cardiac vein leads with a preformed bent tip, as a substitute for a guidewire, as disclosed in U.S. Pat. No. 5,531,781. It has additionally been proposed to provide channels to allow blood flow through the coronary veins in the context of a cardiac vein lead, as disclosed in U.S. Pat. No. 5,800,495. U.S. Pat. Nos. 5,755,766, 5,803,928, 5,755,765, 5,800,495 and 5,531,781, cited above, are incorporated herein by reference in their entireties.

In addition to the placement of electrodes in the great cardiac vein as generally as described in the above-cited patents, it has also been specifically proposed to place cardiac defibrillation electrodes in other cardiac veins. As described in *Gray's Anatomy*, Bounty Books, 1977, the anterior cardiac veins collect blood from the anterior surface of the right ventricle and include the vein of Galen, running along the right border of the heart. The posterior cardiac vein (also referred to as the middle cardiac vein) is described as extending from the apex of the heart to the base of the heart, lying along posterior intraventricular groove (i.e. adjacent the septum). The left cardiac veins are described as collecting blood from the posterior surface of the left ventricle and opening into the lower border of the coronary sinus. A system for deploying electrodes in several of these locations is described in U.S. Pat. No. 5,797,967, also incorporated herein by reference in its entirety, wherein placement of the lead is accomplished by passing the lead through the great cardiac vein, to the apex of the heart, and thereafter passing it in an ascending fashion upward through the anterior or posterior cardiac vein. Placement of an elongated electrode in the middle cardiac vein for purposes of anodal hyperpolarization to enhance cardiac function, following the same implantation procedure, is disclosed in U.S. Pat. No. 5,800,464 issued to Kievel, also incorporated herein by reference in its entirety. U.S Pat. No. 5,935,160 discloses placement of a lead in the "anterior" or "posterior" cardiac veins, however, the illustrated positions of the electrodes appear to correspond to the great cardiac vein and to a left cardiac vein, as described in *Gray's Anatomy*.

SUMMARY OF THE INVENTION

The present invention is directed toward a cardiac defibrillation system including a first, apical defibrillation electrode located in the cardiac venous system, passing around the apex of the ventricle and a second cardiac defibrillation electrode located in the superior vena cava. The system may also include additional defibrillation electrodes, for example a subcutaneous electrode in the form of the conductive housing of an associated implantable cardioverter/defibrillator. The apical electrode may be placed by passing the lead first into the coronary sinus and thereafter either through the great cardiac vein toward the apex of the heart and thereafter upward toward the base of the heart through the middle cardiac vein (lying along the intraventricular groove, adjacent the septum) or through an anterior cardiac vein. Alternatively the electrode may be placed by inserting the lead into the middle cardiac vein and passing it toward the apex of the heart and thereafter passing it upward through the great cardiac vein or an anterior cardiac vein toward the base of the heart. The superior vena cava electrode may be located on a separate lead and may be a conventional superior vena cava type electrode or may be located on the same lead as the apical electrode. Defibrillation pulses are preferably delivered between the apical electrode and the superior vena cava electrode. A third electrode, typically in the form of a subcutaneous electrode which may be the conductive housing of the associated implantable cardioverter/defibrillator may be employed in conjunction with the SVC and atrial electrodes in either a simultaneous pulse fashion wherein the subcutaneous housing is coupled in common with either the apical or SVC electrode or in a sequential pulse fashion wherein two pulses are delivered in sequence, one pulse delivered between the SVC and atrial electrode, a second pulse delivered either between the apical electrode and the subcutaneous electrode or between the SVC electrode and the subcutaneous electrode.

In particular, the inventors have determined that a defibrillation pulse delivery vector between an SVC electrode and an apical electrode located at least partially in the middle cardiac vein provides an opportunity for an improvement in defibrillation energy thresholds as compared to a corresponding pulse delivery vector between a right ventricular defibrillation electrode and an SVC electrode.

DETAILED DESCRIPTION OF THE PREFERRED EMBODIMENTS

Figure 1:
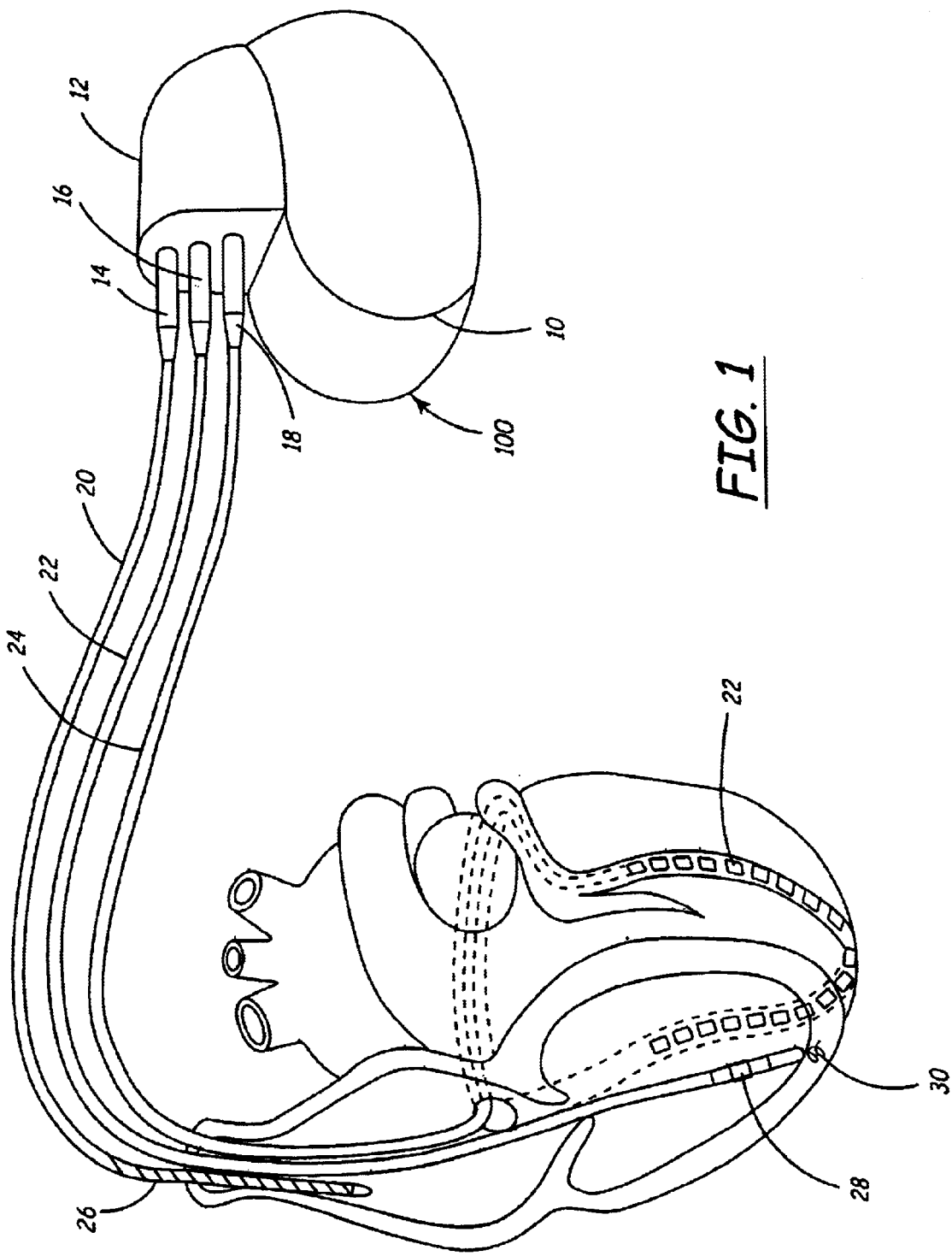
FIG. 1 is a plan view of a cardioversion/defibrillation system according to the present invention having the electrodes located in a first configuration.

FIG. 1 illustrates a first embodiment of a system capable of delivering defibrillation pulses according to the present invention. The system includes an implantable pacemaker/cardioverter/defibrillator 100 which may correspond to any of the commercially available implantable ventricular pacemaker/cardioverter/defibrillators presently on the market, such as the Medtronic JEWEL® and GEMS® devices, the CPI Ventak™ devices, and the Ventritex Cadet™ and Contour™ devices presently available for sale in the United States. Examples of such defibrillators are also disclosed in U.S. Pat. No. 5,447,519 issued to Peterson, U.S. Pat. No. 5,261,400 issued to Bardy and U.S. Pat. No. 5,836,975 issued to DeGroot, all incorporated herein by reference in their entireties.

The defibrillator is provided with a lead system which includes three leads 20, 22 and 24, each of which is provided with a connector assembly 14, 16 and 18, respectively, inserted into connector block 12 of defibrillator 100 in a conventional fashion. The conductive housing 10 of the pacemaker/cardioverter/defibrillator 100 may serve as a subcutaneous cardioversion/defibrillation electrode, as discussed above. In response to detection of tachycardia or fibrillation, pacemaker/cardioverter/defibrillator 100 delivers a cardioversion/defibrillation shock at least between cardioversion/defibrillation electrodes 32 and 26.

Lead 24 carries the apical electrode 32 and is a relatively small diameter lead having a relatively long cardioversion/defibrillation coil electrode 32, for example, extending over a distance of three inches. The lead is preferably 5 French or less in diameter. Any of the lead types as described in the above-cited references for placement in the coronary vein systems may be employed in the context of the present invention as well. In a preferred embodiment, the lead is a "over the wire lead" which passes over a guidewire previously advanced to the desired location in order to facilitate placement of the lead. For example, in the context of a lead system as illustrated in FIG. 1, a guidewire would first be passed through a guide catheter inserted into the coronary sinus and into the great vein, and then passed downward through the great vein to the apex of the heart, and thereafter passed upward into the posterior or middle cardiac vein, lying along the posterior intraventricular groove as illustrated. The cardioversion/defibrillation electrode 32 is preferably placed so that it wraps around the apex of the heart as illustrated.

The second lead 20 is a conventional superior vena cava defibrillation lead of the type currently marketed by Medtronic, Inc. The lead is shown with its cardioversion/defibrillation electrode 26 located in the superior vena cava.

The third lead 22 is a conventional bipolar cardiac pacing lead here illustrated as a screw-in type lead having a helical electrode 30 which may be embedded in the endocardial tissue of the right ventricle and a ring electrode 28. Pacing of ventricular signals and delivery of ventricular cardiac pacing pulses is accomplished using electrodes 28 and 30. In alternate embodiments, a pacing/sensing electrode or electrodes could be added to lead 24 proximal or distal to the cardioversion/defibrillation electrode 32, allowing for lead 22 to be eliminated.

The inventors have determined that placing the lead system according to this method, and in particular placing the lead 20 such that a portion of the defibrillation electrode resides in the middle cardiac vein and preferably also extending around the cardiac apex, provides for improved current distribution. The lead system as so employed therefore also provides an opportunity for reduced defibrillation energy thresholds as compared to delivery of defibrillation pulses between a corresponding superior vena cava electrode and a right ventricular defibrillation electrode.

Figure 2:
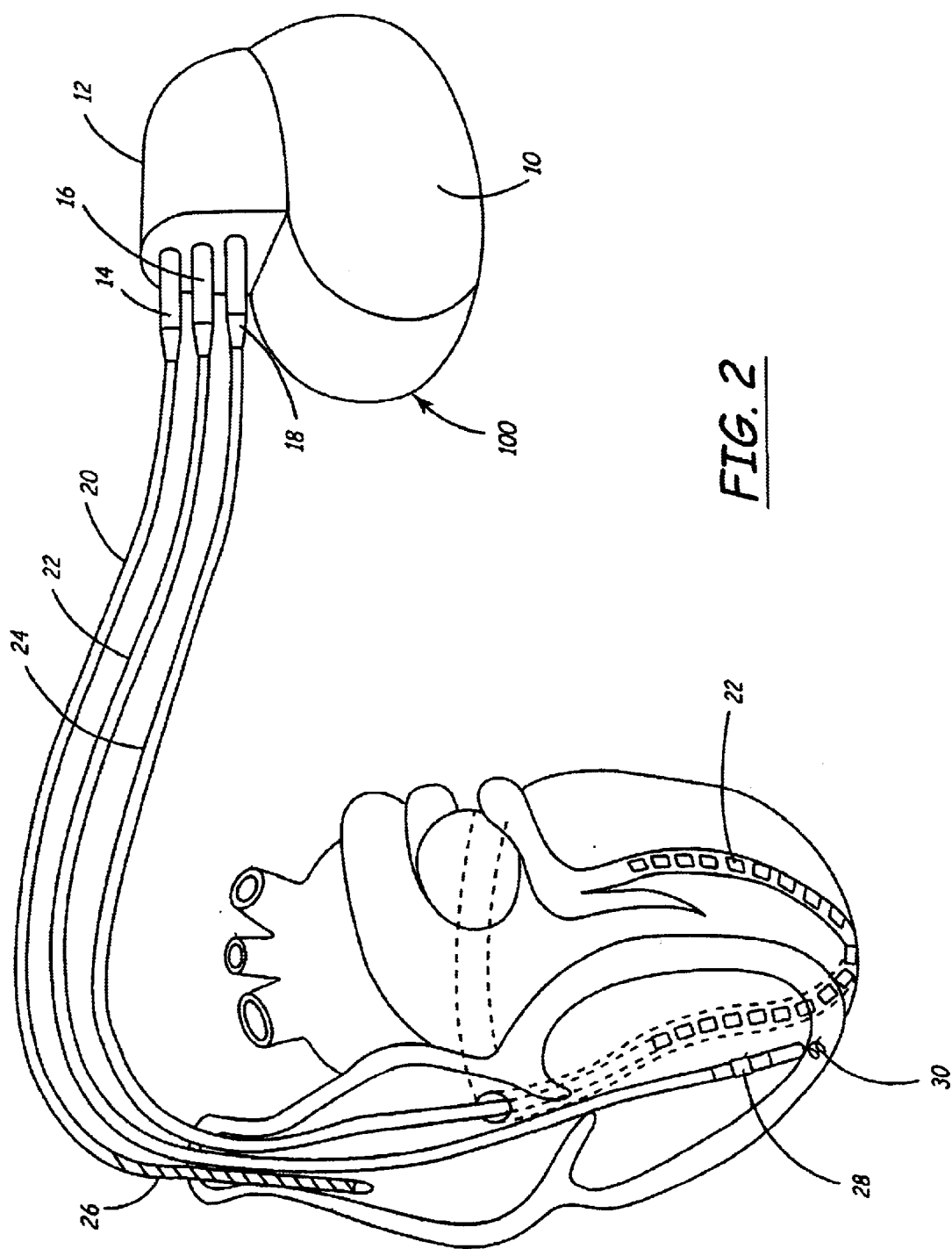
FIG. 2 is a plan view of the same cardioversion/defibrillation system of FIG. 1, with the leads located in a second configuration.

FIG. 2 illustrates the same system as FIG. 1, with the leads located in an alternate configuration. All identically numbered components correspond to those in FIG. 1. In this case, the lead 22 is placed by first passing the guidewire into the coronary sinus and through the middle cardiac vein to the apex of the heart, thereafter advancing the guidewire toward the base of the heart through the great cardiac vein. The lead 22 is thereafter slid over the guidewire and advanced to its desired location and the guidewire is thereafter removed.

Un-illustrated alternative implantation techniques may comprise the insertion of the guidewire into the coronary sinus, thereafter passing it through either the great cardiac vein or through the middle cardiac vein downward toward the apex of the heart, and thereafter passing the guidewire upward through an anterior cardiac vein, and thereafter passing the lead 22 along the guidewire so that at least a distal portion of its electrode resides in an interior cardiac vein.

Figure 3:
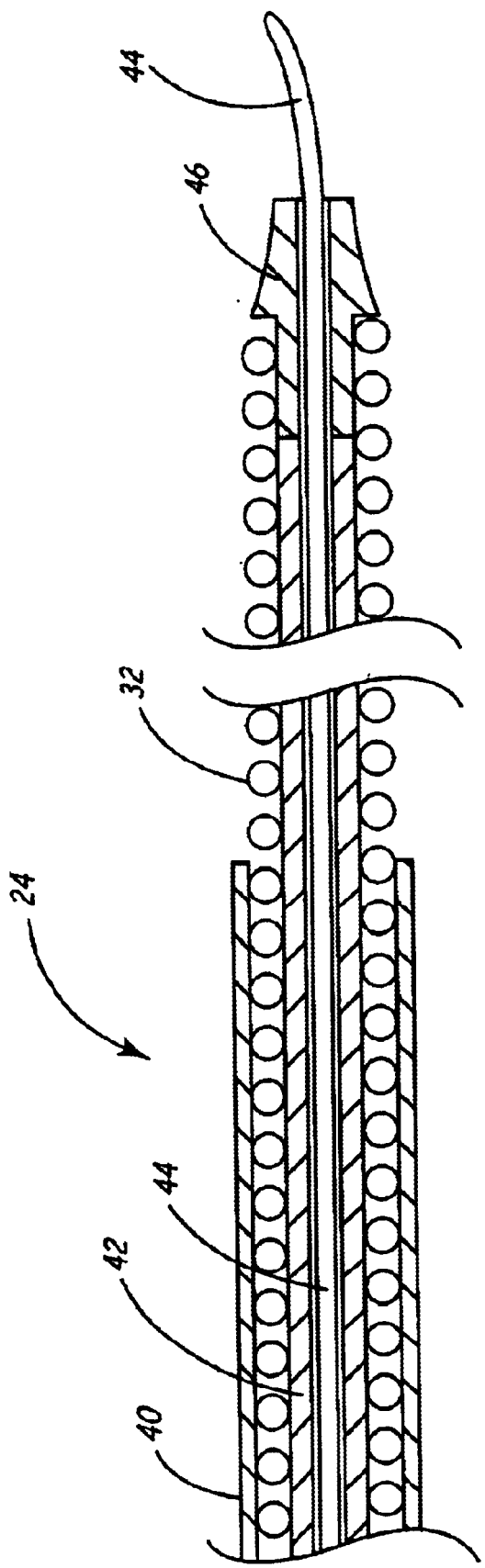
FIG. 3 is a cutaway view through an embodiment of an apical electrical lead appropriate for use in conjunction with the present invention.

FIG. 3 illustrates a side cutaway view through one embodiment of an electrode lead appropriate for use in conjunction with practicing the present invention. Electrode 32 corresponding to electrode 32 in FIGS. 1 and 2 is simply an exposed portion of an elongated coiled conductor running the length of the lead. Electrode/conductor 32 is encased in a thin insulative biocompatible sheath 40, which may be manufactured, for example of polyurethane, silicone rubber or is polytetraflouroethylene. Located within conductor coil/electrode 32, is an inner sleeve 42, which is preferably manufactured of polytetraflouroethylene, through which guidewire 44 passes. Guidewire 44 may be a conventional 0.014-inch diameter guidewire of the sort typically employed for placement of catheters within the cardiac venous or arterial system. At the tip of the lead is a tip member 46 which may be conductive and may be welded to the distal end of electrode/coil 32. While not illustrated, it should be understood that the junction of the inner sleeve 42 and the lead tip 46 may be coupled to one another by means of adhesive, or otherwise, and that the point at which the coil/electrode 32 exits the outer insulative sheath 40 of the device may also similarly be sealed or backfilled by means of a biocompatible adhesive.

In conjunction with the above disclosure, we claim:

1. A method for cardioverting or defibrillating a human heart, comprising:

placing a transvenous lead having a first cardioversion or defibrillation electrode such that the first electrode is located at least partially within the middle cardiac vein of a patient's heart, such that it extends around the apex of the heart;

placing a second cardioversion or defibrillation electrode in a body of the patient; and thereafter delivering a cardioversion or defibrillation pulse between the first and second electrodes.

2. The method of claim 1, wherein placing the transvenous lead having the first electrode comprises advancing the lead through the patient's great cardiac vein toward the apex of the patient's heart and thereafter advancing the lead upward through a cardiac vein, towards the base of the patient's heart.

3. The method of claim 2, wherein advancing the lead upward comprises advancing the lead upward through the patient's middle cardiac vein.

4. The method of claim 1, wherein placing the transvenous lead having the first electrode comprises advancing the lead through the patient's middle cardiac vein toward the apex of the patient's heart and thereafter advancing the lead upward through a cardiac vein, towards the base of the patient's heart.

5. The method of claim 4, wherein advancing the lead upward comprises advancing the lead upward through the patient's great cardiac vein.

6. A method for cardioversion or defibrillating a human heart, comprising:

placing a transvenous lead having a first cardioversion or defibrillation electrode such that the first electrode is located extending around the apex of a patient's heart;

placing a second cardioversion or defibrillation electrode in the superior vena cava of the patient's heart; and thereafter delivering a cardioversion or defibrillation pulse between the first and second electrodes.

7. The method of claim 6 wherein placing the transvenous lead having the first electrode comprises advancing the lead through a first cardiac vein toward the apex of the patient's heart and thereafter advancing the lead upward through a second cardiac vein, towards the base of the patient's heart.

8. The method of claim 7, wherein advancing the lead upward comprises advancing the lead upward through the patient's middle cardiac vein.

9. The method of claim 7, wherein advancing the lead upward comprises advancing the lead upward through the patient's great cardiac vein.

10. The method of claim 7, wherein advancing the lead downward comprises advancing the lead downward through the patient's middle cardiac vein.

11. The method of claim 7, wherein advancing the lead downward comprises advancing the lead downward through the patient's great cardiac vein.

12. A method for cardioverting or defibrillating a human heart, comprising:

placing a transvenous lead having a first cardioversion or defibrillation electrode by advancing the lead through a first cardiac vein toward the apex of the patient's heart and thereafter advancing the lead upward through a second cardiac vein, towards the base of the patient's heart.

placing a second cardioversion or defibrillation electrode in the superior vena cava of the patient's heart; and thereafter delivering a cardioversion or defibrillation pulse between the first and second electrodes.

13. The method of claim 12, wherein advancing the lead upward comprises advancing the lead upward through the patient's middle cardiac vein.

14. The method of claim 12, wherein advancing the lead upward comprises advancing the lead upward through the patient's great cardiac vein.

15. The method of claim 12, Wherein advancing the lead downward comprises advancing the lead downward through the patient's middle cardiac vein.

16. The method of claim 12, wherein advancing the lead downward comprises advancing the lead downward through the patient's great cardiac vein.

17. The method of claim 12, wherein placing the transvenous lead having the first electrode comprises placing the lead such that the first electrode is located extending around the apex of a patient's heart.

18. The method of claim 12, wherein placing the transvenous lead having the first electrode comprises placing the lead such that the first electrode is located at least partially within the middle cardiac vein of the patients heart.

19. The method of claim 12, wherein placing the transvenous lead having the first electrode comprises placing the lead such that the first electrode is located at least partially within the great cardiac vein of the patient's heart.

20. A method for cardioverting or defibrillating a human heart, comprising:

placing a transvenous lead having a first cardioversion or defibrillation electrode such that the first electrode is located at least Partially within the middle cardiac vein of a patient's heart, wherein placing the lead includes advancing the lead through the patient's great cardiac vein toward the apex of the patient's heart and thereafter advancing the lead upward through a cardiac vein, towards the base of the patient's heart;

placing a second cardioversion or defibrillation electrode in a body of the patient; and thereafter delivering a cardioversion or defibrillation pulse between the first and second electrodes.

21. The method of claim 20, wherein placing the transvenous lead having the first electrode comprises placing the first electrode such that it extends around the apex of the heart.

* * * * *